US007306929B2

(12) United States Patent
Ignatov et al.

(10) Patent No.: US 7,306,929 B2
(45) Date of Patent: Dec. 11, 2007

(54) METHOD FOR CONTROLLED RELEASE OF ENZYMATIC REACTION COMPONENTS (75) Inventors: Konstantin Ignatov, Moscow (RU); Vladimir Kramarov, Moscow (RU); Dimitrij Plachov, Ludinghausen (DE)

(73) Assignee: Promega Corporation, Madison, WI (US)

( * ) Notice: Subject to any disclaimer, the term of this patent is extended or adjusted under 35 U.S.C. 154(b) by 468 days.

(21) Appl. No.: 10/817,680

(22) Filed: Apr. 1, 2004

(65) Prior Publication Data

US 2006/0194209 A1    Aug. 31, 2006

(30) Foreign Application Priority Data

Apr. 4, 2003    (DE)    ................ 103 15 640

(51) Int. Cl.
C12Q 1/48    (2006.01)
C12Q 1/68    (2006.01)
C12Q 1/00    (2006.01)
(52) U.S. Cl. .................. 435/15; 435/4; 435/6
(58) Field of Classification Search ............. None
See application file for complete search history.

(56) References Cited

U.S. PATENT DOCUMENTS

| | | | |
|---|---|---|---|
| 3,761,437 A | 9/1973 | Hovey |
| 4,098,728 A | 7/1978 | Rosenblatt |
| 4,186,189 A | 1/1980 | Shalaby et al. |
| 4,247,498 A | 1/1981 | Castro |
| 4,384,975 A | 5/1983 | Fong |
| 4,469,743 A | 9/1984 | Hiss |
| 4,507,414 A | 3/1985 | McRowe et al. |
| 4,519,909 A | 5/1985 | Castro |
| 4,572,833 A | 2/1986 | Pedersen et al. |
| 4,683,195 A | 7/1987 | Mullis et al. |
| 4,683,202 A | 7/1987 | Mullis |
| 4,748,023 A | 5/1988 | Tamas et al. |
| 4,789,630 A | 12/1988 | Bloch et al. |
| 4,830,855 A | 5/1989 | Stewart |
| 4,889,818 A | 12/1989 | Gelfand et al. |
| 5,071,648 A | 12/1991 | Rosenblatt |
| 5,079,352 A | 1/1992 | Gelfand et al. |
| 5,091,187 A | 2/1992 | Haynes |
| 5,108,757 A | 4/1992 | Erdos et al. |
| 5,120,349 A | 6/1992 | Stewart et al. |
| 5,162,057 A | 11/1992 | Akiyama et al. |
| 5,192,675 A | 3/1993 | Chatterjee et al. |
| 5,215,907 A | 6/1993 | Tang et al. |
| 5,229,285 A | 7/1993 | Kajiyama et al. |
| 5,246,707 A | 9/1993 | Haynes |
| 5,283,179 A | 2/1994 | Wood |
| 5,283,189 A | 2/1994 | Takase et al. |
| 5,346,820 A | 9/1994 | Antranikian et al. |
| 5,346,821 A | 9/1994 | Antranikian et al. |
| 5,354,676 A | 10/1994 | Chia et al. |
| 5,374,553 A | 12/1994 | Gelfand et al. |
| 5,380,597 A | 1/1995 | Klang et al. |
| 5,413,926 A | 5/1995 | Oshima et al. |
| 5,427,928 A | 6/1995 | Slesarev |
| 5,432,078 A | 7/1995 | Takase et al. |
| 5,436,149 A | 7/1995 | Barnes |
| 5,455,170 A | 10/1995 | Abramson et al. |
| 5,459,055 A | 10/1995 | Jendrisak et al. |
| 5,466,591 A | 11/1995 | Abramson et al. |
| 5,494,810 A | 2/1996 | Barany et al. |
| 5,500,363 A | 3/1996 | Comb et al. |
| 5,500,370 A | 3/1996 | Jendrisak et al. |
| 5,506,137 A | 4/1996 | Mathur et al. |
| 5,545,552 A | 8/1996 | Mathur |
| 5,565,339 A | 10/1996 | Bloch et al. |
| 5,573,503 A | 11/1996 | Untereker et al. |
| 5,580,573 A | 12/1996 | Kydonieus et al. |
| 5,614,402 A | 3/1997 | Dahlberg et al. |
| 5,616,494 A | 4/1997 | Barnes |
| 5,633,138 A | 5/1997 | Davis et al. |
| 5,643,754 A | 7/1997 | Haake |
| 5,643,777 A | 7/1997 | Antranikian et al. |
| 5,656,463 A | 8/1997 | Slesarev |
| 5,660,854 A | 8/1997 | Haynes et al. |
| 5,662,935 A | 9/1997 | Motta |
| 5,665,551 A | 9/1997 | Gelfand et al. |
| 5,703,379 A | 12/1997 | Le Person et al. |
| 5,705,379 A | 1/1998 | Wilson et al. |
| 5,736,373 A | 4/1998 | Hamilton |

(Continued)

FOREIGN PATENT DOCUMENTS

| | | |
|---|---|---|
| EP | 0572057 A1 | 12/1993 |
| RU | 2215037 | 10/2003 |
| WO | WO 93/16200 A1 | 8/1993 |
| WO | WO 03/012066 A2 | 2/2003 |

OTHER PUBLICATIONS

Aldrich Catalog, p. 1400, (2000-2001).*
Adams, Mark et al., "Complementary DNA Sequencing: Expressed Sequence Tags and Human Genome Project", *Articles*, 1991, p. 1651 only.
Aharoni, Shaul M., "Rigid Backbone Polymers. 2. Polyisocyanates and Their Liquid-Crystal Behavior", *Macromolecules*, vol. 12, No. 1, Jan.-Feb. 1979, pp. 94-103.

(Continued)

*Primary Examiner*—Sandra E. Saucier
(74) *Attorney, Agent, or Firm*—Peter Brunovskis; Brinks Hofer Gilson & Lione (57) ABSTRACT

Compositions and reaction kits are provided for controlling an enzymatic process. The compositions and kits include a substantially water-insoluble, water-permeable polymer and a poorly water-soluble salt of an essential ionic enzymatic reactant. The disclosed compositions and methods are particularly useful for improving the specificity and performance of PCR.

18 Claims, 5 Drawing Sheets

U.S. PATENT DOCUMENTS

| | | | |
|---|---|---|---|
| 5,744,150 | A | 4/1998 | Cercone |
| 5,744,312 | A | 4/1998 | Mamone et al. |
| 5,744,345 | A | 4/1998 | Shimada et al. |
| 5,773,258 | A | 6/1998 | Birch et al. |
| 5,776,720 | A | 7/1998 | Jaffe et al. |
| 5,830,711 | A | 11/1998 | Barany et al. |
| 5,928,665 | A | 7/1999 | Cercone |
| 5,939,257 | A | 8/1999 | Szasz et al. |
| 5,998,195 | A | 12/1999 | Kacian et al. |
| 6,008,025 | A | 12/1999 | Komatsubara et al. |
| 6,027,918 | A | 2/2000 | Mitsuzumi et al. |
| 6,033,859 | A | 3/2000 | Kitabayashi et al. |
| 6,054,564 | A | 4/2000 | Barany et al. |
| 6,113,947 | A | 9/2000 | Cleland et al. |
| 6,130,045 | A | 10/2000 | Wurst et al. |
| 6,143,517 | A | 11/2000 | Young |
| 6,183,998 | B1 | 2/2001 | Ivanov et al. |
| 6,187,573 | B1 | 2/2001 | Imanaka et al. |
| 6,211,289 | B1 | 4/2001 | Tschirner et al. |
| 6,214,557 | B1 | 4/2001 | Barnes et al. |
| 6,251,649 | B1 | 6/2001 | Matsui et al. |
| 6,261,768 | B1 | 7/2001 | Todd et al. |
| 6,280,998 | B1 | 8/2001 | Mathur et al. |
| 6,294,367 | B1 | 9/2001 | Cheng et al. |
| 6,358,726 | B1 | 3/2002 | Takakura et al. |
| 6,380,380 | B1 | 4/2002 | Kaufman |
| 6,403,341 | B1 | 6/2002 | Barnes et al. |
| 6,465,236 | B1 | 10/2002 | Nishino et al. |
| 6,506,410 | B1 | 1/2003 | Park et al. |
| 6,541,216 | B1 | 4/2003 | Wilsey et al. |
| 6,566,109 | B2 | 5/2003 | Kawase et al. |
| 6,576,453 | B2 | 6/2003 | Barany et al. |
| 6,602,677 | B1 | 8/2003 | Wood et al. |
| 6,692,769 | B1 | 2/2004 | Ishibashi et al. |
| 6,787,338 | B2 | 9/2004 | Wittwer et al. |
| 2002/0090618 | A1 | 7/2002 | Smith et al. |
| 2002/0119904 | A1 | 8/2002 | Boskamp et al. |
| 2002/0164751 | A1 | 11/2002 | Short et al. |
| 2003/0027196 | A1 | 2/2003 | Barnes et al. |
| 2003/0068801 | A1 | 4/2003 | Wood et al. |
| 2003/0073113 | A1 | 4/2003 | Van Houten et al. |
| 2003/0082567 | A1 | 5/2003 | Barnes et al. |
| 2003/0113747 | A1 | 6/2003 | Srinivasan et al. |
| 2003/0119150 | A1 | 6/2003 | Ankenbauer et al. |
| 2003/0125385 | A1 | 7/2003 | Cook et al. |
| 2003/0152988 | A1 | 8/2003 | Gelfand et al. |
| 2003/0170867 | A1 | 9/2003 | Young |
| 2003/0232404 | A1 | 12/2003 | Wood et al. |
| 2004/0048308 | A1 | 3/2004 | Barany et al. |

OTHER PUBLICATIONS

Andreas, Susanne et al., "Enhanced efficiency through nuclear localization signal fusion on phage ΦC31-integrase: activity comparison with Cre and FLPe recombinase in mammalian cells", *Nucleic Acids Research*, vol. 30, No. 11, 2000, pp. 2299-2306.

Andruzzi, F. et al., "Studies on Comb-like Polymers. 2. Poly(octadecylethylene oxide)", *Macromolecules*, vol. 13, 1980, pp. 15-18.

Arfin, Stuart et al.. "Eukaryotic methionyl aminopeptidases: Two classes of cobalt-dependent enzymes", *Proc. Natl. Acad. Sci.*, vol. 91, 1995, pp. 7714-7718.

Basu, Soumitra et al., "Biochemical Detection of Monovalent Metal Ion Binding Sites within RNA", *Methods*, vol. 23, 2001, pp. 265-275.

Chandrasena, Gamarallage et al., Use of Response Surfaces to Investigate Metal Ion Interactions in Yeast Fermentations, *J. Am. Soc. Brew. Chem.*, vol. 55. No. 1, 1997, pp. 24-29.

Chou, Quin et al., "Prevention of pre-PCR mis-priming and primer dimerization improves low-copy-number amplifications", *Nucleic Acids Research*, vol. 20, No. 7, 1992, pp. 1717-1723.

Chupov, V.V. et al., "Structure and Physico-Chemical Properties of Comb-Like Polypeptides Based on Poly-L-Lysine", *Polymer Science U.S.S.R.*, vol. 21, 1979, pp. 241-151.

D'Aquila, Richard et al., "Maximizing sensitivity and specificity of PCR by pre-amplification heating", *Nucleic Acids Research*, vol. 190, No. 13, 1991, p. 3749, only.

Elnifro, Elfath et al., "Multiplex PCR: Optimization and Application in Diagnostic Virology", *Clinical Microbiology Reviews*, vol. 13, No. 4, 2000, pp. 559-570.

Erlich. Henry A. et al., "Recent Advances in the Polymerase Chain Reaction", *Science*, vol. 252, 1991, pp. 1643-1650.

Gammons, Christopher H., "The aqueous geochemistry of REE. Part 8: Solubility of ytterbium oxalate and the stability of Yb(III)-oxalate complexes in water at 25° C. to 80° C.", *Chemical Geology*, vol. 166, (2000), pp. 103-124.

Greenberg, Sidney A., "Side Chain Crystallization of n-Alkyl Polymethacrylates and Polyacrylates", *Journal of Chemical Society*, vol. 76, 1954, pp. 6280-6285.

Gromer, Stephan et al., "Active sites of thioredoxin reductases: Why selenoproteins?", *PNAS*, vol. 100, No. 22, 2003. pp. 12618-12623.

Glusker, Jenny et al., "Metal Ions in Biological Systems", *The Rigaku Journal*, vol. 16, No. 2 1999, pp. 8-16.

Handyside, A.H. et al., "Pregnancies from biopsied human preimplantation embryos sexed by Y-specific DNA amplification", *Nature*, vol. 344, 1990, pp. 768-770.

Ignatov, K.B. et al., "A New Approach To Enhanced PCR Specificity", *Russian Journal of Bioorganic Chemistry*, vol. 29, No. 4, 2003, pp. 368-371.

Jackson, J.B., "The polymerase chain reaction in transfusion medicine", *Transfusion*, vol. 30, No. 1, 1990, pp. 51-57.

Jones, Timothy D., "Advanced Binders for High-Tech Applications", printed from the Internet at: <http://www.ceramicindustry.com/ci/cda/articleinformation/coverstory/bncoverstoryitem/0,,100917,00+e.....>, dated Mar. 19, 2004, pp. 1-4.

Jordan, Edmund F. Jr. et al., "Side-Chain Crystallinity. I. Heats of Fusion and Melting Transitions on Selected Homopolymers Having Long Side Chains", *Journal of Polymer Science*, vol. 9 Part A-1, 1971, pp. 1835-1852.

Jordan, Edmund F. Jr. et al., "Side-Chain Crystallinity. II. Heats of Fusion and Melting Transitions of Selected Copolymers Incorporating n-Octadecyl Acrylate or Vinyl Stearate", *Journal of Polymer Science*, vol. 9 Part A-1, 1971, pp. 3349-3365.

Jordan, Edmund F. Jr. et al., "Side-Chain Crystallinity. III. Influence of Side-Chain Crystallinity on the Glass Transition Temperatures of Selected Copolymers Incorporating n-Octadecyl Acrylate or Vinyl Stearate," *Journal of Polymer Science*, vol. 9 Part A-1, 1971, pp. 3367-3378.

Jordan, Edmund F. Jr. et al., "Side-Chain Crystallinity. IV. Mechanical Properties and Transition Temperatures of Copolymers of Methyl Methacrylate with Higher n-Alkyl-Acrylates and N-n-Alkylacrylamides", *Journal of Polymer Science*, vol. 10 Part A-2, 1972, pp. 1657-1679.

Jordan, Edmund F. Jr. et al., "Side-Chain Crystallinity. V. Heats of Fusion and Melting Temperatures on Monomers Whose Homopolymers Have Long Side Chains", *Journal of Polymer Science*, vol. 10, 1972, pp. 3347-3366.

Kaijalainen, S. et al. "An alternative hot start technique for PCR in small volumes using beads of wax-embedded reaction components dried in trehalose", *Nucleic Acids Research*, vol. 21, No. 12, 1993, pp. 2959-2960.

Kellogg, D.E. et al., "TaqStart Antibody™: "Hot Start" PCT Facilitated By A Neutralizing Monoclonal Antibody Directed Against *Taq* DNA Polymerase", *BioTechniques*, vol. 16, No. 6, 1994, pp. 1134-1137.

Kermekchiev, Milko B. et al., "Cold-sensitive mutants of Taq DNA polymerase provide a hot start for PCR", *Nucleic Acids Research*, vol. 31, No. 21. 2003, pp. 6139-6147.

Kovárová, Martina et al., "New Specificity and Yield Enhancer of Polymerase Chain Reactions", *Nucleic Acids Research*, vol. 28, No. 13, 2000, i-iv.

Kulinowski, Kristen et al., "Porous Metals from Colloidal Templates", *Adv. Mater.*, vol. 12, No. 11, 2000. pp. 833-838.

Kumar, Ramesh et al., "Oncogene detection at the single cell level", *Oncogene*, vol. 3, 1988, pp. 647-651.

Lafontaine, Daniel A. et al., "Presence of a coordinated metal ion in a *trans*-acting antigenomic *delta* ribozyme", *Nucleic Acids Research*, vol. 27, No. 15, 1999, pp. 3236-3243.

Lauth, Matthias, "Stable and efficient cassette exchange under non-selectable conditions by combined use of two site-specific recombinases", *Nucleic Acids Research*, vol. 30, No. 21, e115, 2002, pp. 1-7.

McCormick, Frank, "The Polymerase Chain Reaction and Cancer Diagnosis", *Cancer Cells*, vol. 1, No. 2, 1989, pp. 56-61.

Magagnini, P.L., et al., Studies on Comb-like Polymers. 1. Poly(octadecylethylene):, *Macromolecules*, vol. 13, 1980, pp. 12-15.

Miller, Katherine et al., "Improved PCR Amplification Using *Taq*Bead™ Hot Start Polymerase", *Promega Notes Magazine*, No. 60, 1996, pp. 2-5.

Myers, Thomas W., "Reverse Transcription and DNA Amplification by a Thermus thermophilus DNA Polymerase", *Biochemistry*, vol. 30, No. 31, 1991, pp. 7661-7666.

Nelson, Nathan, "Metal ion transporters and homeostasis", *The EMBO Journal*, vol. 18, No. 16, 1999, pp. 4361-4371.

Novak, Jan et al., "Amplification of Flanking Regions: New Applications and Performance Optimization of Single Specific Primer PCR and T-Vector Cloning", *Promega Notes Magazine*, No. 61, 1997, pp. 26-29.

Otsu, Takayuki et al., "Effects of Ortho-Subsituents on Reactivities, Tacticities, and Ceiling Temperatures of Radical Polymerizations of Phenyl Methacrylates", *Journal of Polymer Science: Polymer Chemistry Edition*, vol. 18, 1980, pp. 2197-2207.

Overberger, C.G. et al., "The Preparation and Polymerization of p-Alkylstryrenes. Effect of Structure on the Transition Temperatures of the Polymers", *Journal of Chemical Society*, vol. 75, 1953, pp. 3326-3330.

Palumaa, Peep et al., "Nonoxidative Cadmium-Dependent Dimerization of $Cd_7$-Metallothionen From Rabbit Liver", *Biochemistry*, vol. 31, 1992, pp. 2181-1286.

Pittman, Allen G., "Effect of Polymer Crystallinity on the Wetting Properties of Certain Flouralkyl Acrylates", *Journal of Polymer Science*, vol. 7 Part A-1, 1969, pp. 3053-3066.

Platé, N.A. et al., "Comb-Like Polymers. Structure and Properties", *J. Polymer Sci: Macromolecular Reviews*, vol. 8, 1974, pp. 117-253.

Rabolt, J.F. et al., "Studies of Chain Conformational Kinetics in Poly(di-*n*-alkylsilanes) by Spectroscopic Methods. 1. Poly(di-*n*-hexylsilane), Poly(di-*n*-heptylsilane), and Poly(di-*n*-octylsilane)", *Macromolecules*, vol. 19, 1986, pp. 611-616.

Rossant, Janet et al., ""Cre"-ating mouse mutants-a meeting review on conditional mouse genetics", *Genes and Development*, vol. 13, 1999, pp. 142-145.

Sacramento, Débora et al., "PCR technique as an alternative method for diagnosis and molecular epidemiology of rabies virus", *Molecular and Cellular Probes*, vol. 5, 1991, pp. 229-240.

Scalice, Edward R. et al., "Monoclonal antibodies prepared against the DNA Polymerase from *Thermus aquaticus* are potent inhibitors of enzyme activity", *Journal of Immunological Methods*, vol. 172, 1994, pp. 147-163.

Scott, William G., "Visualizing the structure and mechanism of a small nucleolytic ribozyme", *Methods*, vol. 28, 2002, pp. 302-306.

Sharkey, David J. et al., "Antibodies as Thermolabile Switches: High Temperature Triggering for the Polymerase Chain Reaction", *Bio/Technology*. vol. 12, 1994, pp. 506-509.

Tyagi, Renu et al., "Carbodi-imide coupling of enzymes to the reversibly soluble insoluble polymer Eudragit S-100", *Biotechnol. Appl, Biochem.*, vol. 28, 1998, pp. 201-206.

Voziyanov, Yuri et al., "A dual reporter screening system identifies the amino acid position 82 in Flp site-specific recombinase as a determinant for target specificity", *Nucleic Acids Research*, Vo. 30, No. 7, 2002, pp. 1656-1663.

Wages, John M., Jr. et al., "Clinical Performance of a Polymerase Chain Reaction Testing Algorithm for Diagnosis of HIV-1 Infection in Peripheral Blood Mononuclear Cells", *Journal of Medical Virology*, vol. 33, 1991, pp. 58-63.

Watanabe, Junji et al, "Thermotropic Polypeptides. 2. Molecular Packing and Thermotropic Behavior of Poly(L-glutamates) with Long *n*-Alkyl Side Chains", *Macromolecules*, vol. 18, 1985, pp. 2141-2148.

Welch, Simon, G. et al., "*Taq*52 1, a novel and thermostable Type II restriction endonuclease from the genus Thermus, recognising the pentanucleotide sequence GC(A or T)GC and cleaving DNA between the first and second bases of the recognition sequence: G↓C(A or T)GC", *Nucleic Acids Research*, vol. 23, No. 22, 1995, pp. 4573-4575.

Wernars, K. et al., "Successful Approach for Detection of Low Numbers of Enterotoxigenic *Escherichia coli* in Minced Meat by Using the Polymerase Chain Reaction", *App.Environ. Microbiol.*, vol. 57, No. 7, 1991, pp. 1914-1919.

Yokota, Kenji et al., "Widely-Spaced Comb-Like Polymers Having Fluoroalkyl Side Chains", *Polmer Journal*, vol. 17, No. 9, 1985, pp. 991-996.

International Search Report for corresponding PCT application No. PCT/US2004/010168, dated Oct. 13, 2004, 2 pages.

\* cited by examiner

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Primer P1

<400> SEQUENCE: 1
atggctaacg aattaacctg gca                                            23

<210> SEQ ID NO 2
<211> LENGTH: 22
<212> TYPE: DNA
<213> ORGANISM: Artificial Sequence
<220> FEATURE:
```

```
<223> OTHER INFORMATION: Primer P2

<400> SEQUENCE: 2
ttactcactc tctgccggta at                                        22
```

METHOD FOR CONTROLLED RELEASE OF ENZYMATIC REACTION COMPONENTS

BACKGROUND

This application claims the benefit of priority under 35 U.S.C. § 119 to German application DE 103 15 640.2, filed Apr. 4, 2003.

In biomolecular processes it is often important to control the activity of an enzyme. This is particularly the case with DNA polymerase enzymes used for the polymerase chain reaction (PCR). PCR reactions oftentimes involve the use of a $Mg^{2+}$-dependent heat-resistant DNA polymerase enzyme (such as Taq DNA polymerase) in a multi-cycle process employing several alternating heating and cooling steps to amplify DNA (U.S. Pat. Nos. 4,683,202 and 4,683,195). First, a reaction mixture is heated to a temperature sufficient to denature the double stranded target DNA into its two single strands. The temperature of the reaction mixture is then decreased to allow specific oligonucleotide primers to anneal to their respective complementary single stranded target DNAs. Following the annealing step, the temperature is raised to the temperature optimum of the DNA polymerase being used, which allows incorporation of complementary nucleotides at the 3' ends of the annealed oligonucleotide primers thereby recreating double stranded target DNA. Using a heat-stable DNA polymerase, the cycle of denaturing, annealing and extension may be repeated as many times as necessary to generate a desired product, without the addition on polymerase after each heat denaturation. Twenty or thirty replication cycles can yield up to a million-fold amplification of the target DNA sequence ("Current Protocols in Molecular Biology," F. M. Ausubel et al. (Eds.), John Wiley and Sons, Inc., 1998).

Although PCR technology has had a profound impact on biomedical research and genetic identity analysis, amplification of non-target oligonucleotides and mispriming on non-target background DNA, RNA, and/or the primers themselves, still presents a significant problem. This is especially true in diagnostic applications where PCR is carried out in a milieu of complex genetic backgrounds where the target DNA may be proportionately present at a very low level (Chou et al., Nucleic Acid Res., 20:1717-1723 (1992).

A chief problem is that even though the optimal temperature for Taq DNA polymerase activity is typically in the range of 62°-72° C., significant activity can also occur between 20°-37° C. (W. M. Barnes, et al, U.S. Pat. No. 6,403,341). As a result, during standard PCR preparation at ambient temperatures, primers may prime extensions at non-specific sequences because only a few base pairs at the 3'-end of a primer which are complementary to a DNA sequence can result in a stable priming complex. As a result, competitive or inhibitory products can be produced at the expense of the desired product. Thus, for example, structures consisting only of primers, sometimes called "primer dimers" can be formed by Taq DNA polymerase activity on primers inappropriately paired with each other.

The probability of undesirable primer-primer interactions also increases with the number of primer pairs in a reaction, particularly in the case of multiplex PCR. Mispriming of template DNA can also result in the production of inhibitory products or "wrong bands" of various lengths. During PCR cycling, non-specific amplification of undesired products can compete with amplification of the desired target DNA for necessary factors and extension constituents, such as dNTPs, which can lead to misinterpretation of the assay.

Given the sensitivity of Taq DNA polymerase and its propensity to progressively amplify relatively large amounts of DNA from any primed event, it is imperative to control Taq DNA polymerase activity to prevent production of irrelevant, contaminating DNA amplification products, particularly when setting up PCR reactions.

Undesirable PCR side reactions typically occur during PCR preparation at ambient temperatures. One approach for minimizing these side reactions involves excluding at least one essential reagent (dNTPs, $Mg^{2+}$, DNA polymerase or primers) from the reaction until all the reaction components are brought up to a high (e.g., DNA denaturation) temperature; the idea is to prevent binding of primers to one another or to undesired target sequences (Erlich, et al, Science 252, 1643-1651, 1991; D'Aquila, et al, Nucleic Acids Res. 19, 3749, 1991). This is an example of a "physical" PCR hot-start approach where an essential component is physically withheld until a desired reaction temperature is reached.

Other physical hot-start approaches have been described that physically segregate the reaction components from each other to guarantee that DNA polymerase activity is suppressed during the period preceding PCR initiation (see e.g., U.S. Pat. No. 5,643,764; Russian patent RU 2,215,037) or that employ the "chemical/biochemical hot-start" methods that utilize modified DNA polymerases reversibly activatable upon heating (e.g., AMPLITAQ GOLD™ DNA POLYMERASE, PE Applied Biosystems) or monoclonal, inactivating antibodies against Taq DNA polymerase that are bound to the polymerase at ambient temperatures (Scalice et al., J. Immun. Methods, 172: 147-163, 1994; Sharkey et al., Bio/Technology, 12:506-509, 1994; Kellogg et al., Biotechniques, 16: 1134-1137, 1994).

The different PCR hot-start approaches have multiple shortcomings. Physical hot-start methods are plagued by contamination problems, plugging up of pipet tips with wax or grease and increased heating times. Chemical/biochemical hot-start methods can damage the template DNA and can require prohibitively excessive amounts of expensive anti-Taq antibodies.

Accordingly, there is a need in the art for new PCR hot-start methods minimizing or eliminating the many problems or shortcomings associated with the prior art procedures. More generally, there is a need for new approaches for controlling other Mg-dependent enzymes or other non-Mg-dependent enzymes where controlled activity is desired.

SUMMARY

In one aspect, the present invention provides compositions and methods for controlling an enzymatic process in which a substantially water-insoluble, water-permeable polymer and a poorly water-soluble salt of an ionic enzymatic reactant are combined to form a composition providing controlled release of the ionic enzymatic reactant. The water-insoluble/water-permeable polymer is designed to facilitate electrostatic interaction(s) with a cationic group in the salt and to act as a diffusion barrier for release of the ionic reactant into a surrounding reaction medium. The salt is chosen to have low solubility in water, so that its sequestration and release from the polymer can occur in a controlled manner, depending on varying enzymatic reaction conditions, such as temperature, incubation time and/or pH. In effect, the polymer provides a diffusion barrier for the controlled release of an essential ionic enzymatic reactant from the salt, whose dissociation and release from the polymer is further determined by e.g. solubility of the salt and/or temperature in the reaction medium.

In another aspect, a composition containing a substantially water-insoluble, water-permeable polymer and a poorly water-soluble salt are incorporated in a reaction vessel or on a reaction surface and/or in a reaction kit for controlling an enzymatic process. Specifically, methods are provided for preparing and using reaction vessels coated with a salt of an ionic enzymatic reactant entrapped in water-insoluble/water-permeable polymers, such as poly(vinyl acetal) resins. The coated reaction vessels may be used to regulate enzymatic processes, such as those involving heat-stable DNA polymerase enzymes in PCR reactions.

A salt of the ionic enzymatic reactant may include a monovalent, divalent or polyvalent metal ion from magnesium, manganese, cadmium, calcium, cobalt, copper, iron, lead, molybdenum, mercury, nickel, potassium, sodium or zinc. Preferred embodiments include compositions and coated reaction vessels or surfaces used to control metal ion-dependent enzyme activities. Exemplary compositions or reaction kits include magnesium ions or magnesium salts, such as magnesium oxalate, entrapped in poly(vinyl acetal) resins for regulating $Mg^{2+}$-dependent enzyme activities.

The reaction vessel, surface or kit may contain additional reaction component(s). Further, the reaction kit can contain a plurality of additional reaction vessels, each containing at least one additional reaction component. Among the additional reaction components, one may include an enzyme (such as a heat-stable polymerase for PCR) whose activity is dependent on release and/or dissociation of an ionic reactant (such as a metal ion) from both the polymer and the salt.

Other features, aspects and advantages of the invention will be, or will become, apparent to one with skill in the art upon examination of the following figures and detailed description. It is intended that all such additional systems, features, aspects and advantages included within this description, are within the scope of the invention, and are protected by the following claims.

BRIEF DESCRIPTION OF THE FIGURES

These and other features, aspects, and advantages of the present invention will become better understood with regard to the following description, claims and accompanying drawings where:

DETAILED DESCRIPTION

In order to provide a clear and consistent understanding of the specification and claims, the following definitions are provided.

"Low solubility in water," "poorly soluble" and "poorly water-soluble" are used interchangeably herein to designate a salt having a molar solubility in water less than about $1\times10^{-3}$ mol/L at 25° C.

"Ionic enzymatic reactant" and "ionic reactant" are used interchangeably herein to designate an ionic cofactor or ionic substrate reagent necessary, but not necessarily sufficient for activating an enzyme (by itself). The ionic cofactor or substrate may constitute a cationic reactant, including, but not limited to e.g., a metal ion or it may constitute an anionic reactant, including, but not limited to e.g., ATP, nucleotides, nucleosides, etc.

"Thermostable", "thermally stable" and "heat-stable" are used interchangeably herein to describe enzymes which can withstand temperatures up to at least 95° C. for several minutes without becoming irreversibly denatured. Typically, such enzymes have an optimum temperature above 45° C., preferably between 50° to 75° C.

In one aspect, the present invention provides a composition and a method for controlling an enzymatic process in which a substantially water-insoluble, water-permeable polymer and a salt of an ionic enzymatic reactant having low solubility in water are combined to provide controlled release of the ionic enzymatic reactant. The water-insoluble/water-permeable polymer may be chosen to facilitate electrostatic interaction(s) with a cationic group in the salt. While not intending to be limiting, it is believed that the polymer may reduce the diffusion coefficients of a poorly soluble salt, slowing down its distribution and release. In effect, the polymer provides a diffusion barrier for dissociation and/or release of the essential ionic enzymatic reactant from the salt. Dissociation and/or release of the ionic enzymatic reactant from the salt into the surrounding reaction medium may be further determined by physical characteristics of the salt itself (e.g., solubility) or reaction conditions affecting solubility of the salt (e.g., temperature, time and/or pH). By controlling the concentration and release characteristics of the ionic enzymatic reactants, the present invention provides a means for controlling enzymatic processes, including, but not limited to, the start of an enzymatic process.

In one aspect, the present invention provides a reaction mixture containing a substantially water-insoluble, water-permeable polymer and a poorly soluble salt of an ionic enzymatic reactant for controlling enzymatic processes. The reaction mixture may be coated onto the wall of a reaction vessel provided in a reaction kit for controlling an enzymatic process. The vessel or kit may include a first reaction vessel containing the polymer/salt mixture and may further include one or more additional reaction components to facilitate the enzymatic process. Alternatively, the reaction kit may include a plurality of additional reaction vessels, each containing at least one additional reaction component to facilitate an enzymatic process.

Methods for preparing and using reaction vessels for controlling an enzymatic process are also provided in which a water-insoluble, water-permeable polymer and a poorly soluble salt of an ionic enzymatic reactant are added to a reaction vessel. Additional steps include incorporation of additional reaction component(s), including the enzyme, and adjusting the reaction conditions to permit sequestration of the ionic enzymatic reactant under a first reaction condition and release of the ionic enzymatic reactant into the surrounding reaction medium under a second reaction condition (e.g., increased temperature) to activate and/or complete an enzymatic process.

Polyvinyl acetal polymers are a preferred class of water-insoluble/water-permeable polymers for use in the present invention. A particularly preferred embodiment is a poly (vinyl butyral) polymer, such as poly (vinyl butyral-co-vinyl alcohol-co-vinyl acetate) (e.g., Sigma-Aldrich Co., Product Number 41,841-2). This polymer may be made by condensing poly(vinyl alcohol) with butyraldehyde in the presence of an acid catalyst, such as sulfuric acid (see "Textbook of Polymer Science," $3^{rd}$ ed., F. W. Billmeyer (Ed.), John Wiley and Sons, Inc., 1984). The reaction may be carried out by starting with an aqueous mixture of poly(vinyl alcohol) and adding butyraldehyde and acid catalyst to form a poly(vinyl butyral) precipitate. Adjacent alcohol groups react with butyraldehyde to form ether bonds linked to an aliphatic butyl chain. The condensation reaction may be stopped when the hydroxyl groups are reacted to form a sufficient number of linked ether bonds.

When reacting poly(vinyl alcohol) with an aldehyde in the condensation reaction, an aliphatic chain from butyraldehyde extends from the carbon in an ether linkage to the carbons that were bound to the two reactive alcohol groups above. The aliphatic extension can be represented by the formula, $C_nH_{2n+1}$. Alternate resins within the scope of the present invention may include other poly(vinyl acetals) in which poly(vinyl alcohol) is reacted with aldehydes, other than butyraldehyde. With butyraldehyde, the attached aliphatic chain has the formula $C_3H_7$. However, poly(vinyl alcohol) may also be reacted with other aldehydes, such as formaldehyde, to produce a poly(vinyl formal) resin having a $C_1H_3$ extension. Other aldehydes may be used to produce other polyvinyl acetals having different $C_nH_{2n+1}$ extensions. Suitable $C_nH_{2n+1}$ extensions may be synthesized where n=1-20.

While not intending to be bound by any theory, it is believed that the water-insoluble/water-permeable polymers of the present invention provide a diffusion barrier for ionic enzymatic reactant availability in a reaction medium. This barrier may be electrostatic and/or physical. For example, charged groups in the salt may mediate electrostatic interactions with the water-insoluble, water-permeable polymer so that the complexed ionic enzymatic reactant is preferentially sequestered by the polymer in a first reaction condition, but released from the polymer in a second reaction condition. In particular, it is believed that oxygen atoms in the acetal ring of poly(vinyl) acetal polymers facilitate electrostatic interactions with cationic groups (such as $Mg^{2+}$) in salts having low solubility in water. In addition, it is believed that increased temperatures increase the permeability of substances associated with water-insoluble water-permeable polymers. Consequently, the water-insoluble, water-permeable polymers of the present invention are believed to provide a diffusion barrier for salts of ionic enzymatic reactants.

An ionic enzymatic reactant mediating electrostatic interactions with the water-insoluble, water-permeable polymer may be itself necessary for initiating or completing an enzymatic process. Alternatively, a counter-ion may be mediating the electrostatic interaction with the polymer, thereby indirectly influencing the dissociation and release of an ionic enzymatic reactant directly involved in the enzymatic process.

The water-insoluble, water-permeable polymers of the present invention may contain variable amounts of monomer in a given polymer. For example, polyvinyl acetals may contain between about 5-40% polyvinyl alcohol, preferably between about 10-30%, more preferably between about 15-25%, or most preferably between about 15-20% polyvinyl alcohol. Polyvinyl acetals may also contain less than about 5% poly(vinyl acetate), less than about 3%, between about 0.3-2.5% or between about 0.3-1.5% poly(vinyl acetate). Monomer ratios for water-insoluble, water-permeable polymers may be adjusted to optimize controlled release of ionic enzymatic reactants.

Exemplary polyvinyl acetals include polyvinyl butyral, polyvinyl polyvinyl formal, combinations, blends, and copolymers thereof, and the like. Alkyl ester containing polymer resins, such as polyvinvyl esters and alkyl polyesters may also be incorporated in the polymers of the present invention. Examples of polyvinyl esters include polyvinyl acetate, polyvinyl butyrate, etc. Examples of alkyl polyesters include, but are not limited to, poly(lactide), poly (glycolide), copolymers thereof, and the like.

Poly(vinyl alcohols) used to synthesize the polymers of the present invention may be further engineered to include monomers having structures resembling acetate to further optimize the physical and chemical characteristics of the resulting polymer. For example, vinyl acetate may be polymerized to form poly(vinyl acetate), a precursor to poly (vinyl alcohol) in the formation of e.g., poly (vinyl butyral-co-vinyl alcohol-co-vinyl acetate). However, other monomers may be copolymerized with vinyl acetate, including, but not limited to, acrylonitrile, polyacylonitrile, acrylamide, acrylic acid, methacrylic acid, methacrylate, methyl methacrylate, 2-hydroxy ethyl methacrylate, glycidyl methacrylate, ethylene glycol dimethacrylate, combinations, blends, and copolymers thereof, and the like.

Included within the scope of the present invention are the water-insoluble, water-permeable polymers disclosed and prepared in accordance with the disclosure set forth in U.S. Pat. No. 4,247,498, the contents of which are expressly incorporated by reference in their entirety. Suitable water-insoluble, water-permeable polymers for use in the present invention may include, but are not limited to, non-acrylic polyolefins, such as low density polyethylene, high density polyethylene, polypropylene, polystyrene, polyvinylchloride, acrylonitrile-butadiene-styrene terpolymers, styrene-acrylonitrile copolymer, styrene butadiene copolymers, poly (4-methyl-pentene-1), polybutylene, polyvinylidene chloride, polyvinyl butyral, chlorinated polyethylene, ethylene-vinyl acetate copolymers, polyvinyl acetate, polyvinyl alcohol, and combinations and blends thereof, acrylic polyoflefins, such as polymethyl-methacrylate, polymethyl-acrylate, ethylene-acrylic acid copolymers, ethylene-acrylic acid metal salt copolymers, and combinations and blends thereof; oxidation polymers, including polyphenylene oxide; and condensation polymers including polyethylene terephthalate, polybutylene terephthalate, Nylon 6, Nylon 11, Nylon 13, Nylon-6,6, polycarbonates, polysulfone, and combinations and blends thereof.

Further included within the scope of the invention are the water-insoluble, water-permeable controlled release polymers disclosed and prepared in accordance with the disclosure set forth in U.S. Pat. No. 5,580,573, the contents of which are expressly incorporated by reference in their entirety. Suitable water-insoluble, water-permeable polymers for use in the present invention may include, but are not limited to, poly(ethyl methacrylate), poly(n-propyl methacrylate) and poly(isobutyl methacrylate).

Also included within the scope of the invention are the water-insoluble, water-permeable temperature-controlled side-chain crystallizable polymers disclosed and prepared and/or cross-linked in accordance with the disclosure set forth in U.S. Pat. No. 4,830,855, the contents of which are expressly incorporated by reference in their entirety. Suitable water-insoluble, water-permeable polymers for use in the present invention may include, but are not limited to, side-chain crystallizable polymers (sometimes called "comb-like" polymers; reviewed in J. Poly. Sci.: Macromol. Rev. (1974) 8: 117-253) or cross-linked side-chain crystallizable polymers substantially impermeable to agents below the melt temperature, but substantially permeable to agents above the melt temperature, including, but not limited to, recrystallized poly(vinyl stearate) (PVS), polyoctadecyl acrylate (PODA), Elvax 40, Elvax 250, polymethyltetradecyl siloxane; acrylate, fluoroacrylate, methacrylate and vinyl ester polymers (also described in J. Poly. Sci. (1972) 10: 3347; J. Poly. Sci. (1972) 10: 1657; J. Poly. Sci. (1971) 9: 3367; J. Poly. Sci. (1971) 9: 3349; J. Poly. Sci. (1971) 9: 1835; J.A.C.S. (1954) 76: 6280; J. Poly. Sci. (1969) 7: 3053; Polymer J. (1985) 17: 991); corresponding acrylamides, substituted acrylamide and maleimide polymers (also described in J. Poly. Sci., Poly. Physics Ed. (1980) 18: 2197); polyalphaolefin polymers (also described in J. Poly. Sci.: Macromol. Rev. (1974) 8: 117-253 and Macromolecules (1980) 13: 12); polyalkylvinylethers, polyalkylethylene oxides (also described in Macromolecules (1980) 13: 15); alkylphosphazene polymers, polyamino acids (also described in Poly. Sci. USSR (1979) 21: 241, Macromolecules (1985) 18: 2141), polyisocyanates (also described in Macromolecules (1979) 12: 94); polyurethanes made by reacting amine- or alcohol-containing monomers with long chain alkyl isocyanates, polyesters and polyethers, polysiloxanes and polysilanes (also described in Macromolecules (1986) 19: 611) and p-alkylstyrene polymers (also described in J.A.C.S. (1953) 75: 3326 and J. Poly. Sci. (1962) 60: 19).

The amount of polymer for use in a reaction vessel may depend on the size of the reaction vessel and the volume of the reaction mixture. Small reaction tubes (e.g., 20, 50, 100, 200, 500 µl Eppendorf tubes) for PCR reactions involving e.g, 100 µl reaction volumes, may accommodate a range of resin amounts. By way of example, poly(vinyl butyral) resins (e.g., poly(vinyl butyral-co-vinyl alcohol-co-vinyl acetate) for PCR may employ 0.02-2.5 mg-, preferably 0.03-1.0 mg- and still more preferably 0.3-0.5 mg- or 0.03-0.10 mg/reaction tube/100 µl reaction volume. Other substantially water-insoluble, water-permeable polymer amounts may be extrapolated from these amounts, or they may be empirically determined by those of skill in the art based on the a variety of factors, including, but not limited to, enzyme reaction volume, amount of free ionic reactant necessary for the enzymatic reaction, salt release characteristics of the polymer, salt solubility and dissociation characteristics, salt release and dissociation characteristics as a function of temperature and/or pH, molecular weight of polymer, etc.

Stock solutions of the water-insoluble, water-permeable polymers may be prepared by dissolving the polymer in a suitable solvent. A range of resin concentrations may be prepared including, but not limited to 1.5-50 mg/ml. A preferred concentration is 10-20 mg/ml. Suitable solvents for suspending the water-insoluble, water-permeable polymers include chloroform, ethanol, glacial acetic acid, acetone, methylene chloride, DMSO and the like. Chloroform and ethanol are particularly preferred solvents for poly(vinyl butyral) resins, such as poly(vinyl butyral-co-vinyl alcohol-co-vinyl acetate).

Salts for use in the present invention include salts of essential ionic enzymatic reactants having low solubility in water so as to facilitate sequestration or release of the ion reactant from the polymer in a controlled manner, depending on enzymatic reaction conditions, such as temperature, incubation time and/or pH. The ionic enzymatic reactants are temporarily rendered water-insoluble by complexation with cationic or anionic counter-ions. Cations or anions may be monomeric or polymeric.

Cationic reactants for use in the present invention may include free monovalent, divalent or polyvalent cations, including, but not limited to metal ions from magnesium, manganese, cadmium, calcium, chromium, cobalt, copper, iron, lead, mercury, molybdenum, nickel or zinc. Preferred cationic reactants in this list, include, but are not limited to $Mg^{2+}$, $Mn^{2+}$, $Zn^{2+}$, $Ca^{2+}$, $Cd^{2+}$, $Cu^{2+}$, $Co^{2+}$, $Cr^{2+}$, $Cr^{3+}$, $Cr^{6+}$, $Ni^{2+}$, $Ni^{3+}$, $Pb^{2+}$, $Pb^{4+}$, $Fe^{2+}$, $Fe^{3+}$ and $Hg^{2+}$. Suitable monovalent cationic reactants may include, but are not limited to $Na^+$, $K^+$, $NH_4^+$, Other cationic reactants may include $NAD^+$, $NADP^+$ and the like.

Cations may be rendered less water soluble by complexation with anions, including, but not limited to, halide, nitrate, citrate, maleate, sulfate, acetate, oxalate, malonate, succinate, glutarate, fumarate, benzoate, phthalate, isophthalate, terephthalate, malate, tartarate, pyrophosphate, formate, isocitrate, ethylenedinitrilotetra-acetate, 1,2,3,4-butane tetracarboxylate, benzoate, hemimellitate, trimellitate, trimesate, pyromellitate, mellitate, mesaconate, mesaconate2-naphthylenesulfonate (napsylate), gluconate, 1,1' methylene bis (2-hydroxy-3-naphthalene) carboxylic acid (pamoate), tolylsulfonate (tosylate), methanesulfonate (mersylate), glucoheptanoate (gluceptate), bitartrate, polyglutamic acid and/or behenate (anionic form of waxy fatty acid).

Anionic reactants may include various nucleosides or nucleoside derivatives, including but not limited to ATP, ADP, pyrophosphate, nucleotides, deoxynucleotides, ribonucleotides, deoxyribonucleotides, dideoxyribonucleotides, oligonucleotides, Coenzyme A, anionic radicals, and the like.

Anionic reactants may be rendered less water soluble by complexation with cations, but not limited to metal ions, calcium, magnesium or their 1:1 fatty acid salts; various amines, including dibenzylethylenediamine (benzathine), N,N' (dihydroabietyl)ethylene diamine (hydrabamine) or polymers such as polylysine.

Salts for use in the present invention have low solubility in water. The salts may have molar solubilities in water at 25° C. of less than about $1\times10^{-2}$, less than about $1\times10^{-3}$, less than about $1\times10^{-4}$ mol/L or less than about $1\times10^{-5}$ mol/L. Preferably, the solubility of the salt is between about $1\times10^{-3}$ mol/L and $1\times10^{-8}$ mol/L, between about $5\times10^{-4}$ mol/L and $5 \times 10^{-5}$ mol/L, between $1 \times 10^{-5}$ mol/L and $1 \times 10^{-6}$ mol/L or a combination of solubility ranges thereof.

Preferably the salts exhibit temperature dependent solubility in water in which the solubility increase in water between 15°-60° C. or 25°-50° C. is at least 2-fold, preferably 4-fold or even 10-fold or where the solubility in water between 15°-100° C. or 25°-90° C. is at least 4-fold, preferably at least 10-fold or even 30-fold.

Altering the reaction conditions (increasing incubation times, increasing temperature or changing the pH) can affect solubility of the salt by extension, dissociation and/or release of free ions. Accordingly, salts may be selected based on their dissociation rate in an enzymatic reaction medium. In a specific aspect, salts may be selected based on their ability to retain ionic enzymatic reactants in a complexed state at a lower temperature (to prevent appreciable or detectable enzyme activity), and to promote dissociation and/or release of free ionic enzymatic reactants at a higher temperature to activate and complete the enzymatic process (provided that all other necessary reaction components are present in the reaction medium).

The salts may include anhydrous forms or hydrated forms, such as hemihydrates, dihydrates, trihydrates, and the like. Salts having the above characteristics are described in e.g., the CRC Handbook of Chemistry and Physics, $82^{nd}$ Edition, D. R. Lide (ed), The Chemical Rubber Company, 2001. Conventional methodologies known to those skilled in the art can be utilized to empirically determine or verify solubilities.

The salts may be suspended in the polymer resin suspensions and/or coated onto the wall of a reaction vessel or onto a reaction surface by lyophilization. Additional reaction components (e.g., enzymes, substrates, etc.) may be incorporated into the suspensions and/or wall coatings.

Preferred salts for use with magnesium-dependent enzymes, include, but are not limited to magnesium sulfite ($MgSO_3$), magnesium oxalate ($MgC_2O_4$), magnesium fluoride ($MgF_2$), magnesium tungstate ($MgWO_4$), and combinations thereof.

Preferred salts for use with manganese-dependent enzymes, include, but are not limited to manganese II iodate ($Mn(IO_3)_2$), manganese II oxalate ($MnC_2O_4$), manganese II tungstate ($MnWO_4$), and combinations thereof.

Preferred salts for use with calcium-dependent enzymes, include, but are not limited to calcium tungstate ($CaWO_4$), calcium hydrogen phosphate ($CaHPO_4$), calcium sulfite ($CaSO_3$), calcium fluoride ($CaF_2$), calcium carbonate ($CaCO_3$), calcium oxalate ($CaC_2O_4$), calcium hydroxide ($Ca(OH)_2$), calcium iodate ($Ca(IO_3)_2$) and combinations thereof.

Preferred salts for use with copper-dependent enzymes, include, but are not limited to copper II fluoride ($CuF_2$), copper II iodate ($Cu(IO_3)_2$), copper II molybdate ($CuMoO_4$), copper I chloride ($CuCl$), copper II oxalate ($CuC_2O_4$), copper I bromide ($CuBr$) and combinations thereof.

Preferred salts for use with iron-dependent enzymes, include, but are not limited to iron TI oxalate ($FeC_2O_4$), iron II fluoride ($FeF_2$) and combinations thereof.

Preferred salts for use with lead-dependent enzymes, include, but are not limited to lead II bromide ($PbBr_2$), lead II fluoride ($PbF_2$), lead II iodide ($PbI_2$), lead II thiocyanate ($Pb(SCN)_2$), lead II tungstate ($PbWO_4$), lead II sulfate ($PbSO_4$), lead II oxalate ($PbC_2O_4$) and combinations thereof.

A preferred salt for molybdenum-dependent enzymes, includes, but is not limited to molybdenum VI oxide ($MoO_3$).

Preferred salts for use with nickel-dependent enzymes, include, but are not limited to nickel II iodate ($Ni(IO_3)_2$), nickel II carbonate ($NiCO_3$) and combinations thereof.

Preferred salts for use with potassium-dependent enzymes, includes, but are not limited to potassium periodate ($KIO_4$).

Preferred salts for use with sodium-dependent enzymes, include, but are not limited to sodium tellurate ($Na_2TeO_4$), sodium hexafluorosilicate ($Na_2SiF_6$) and combinations thereof.

Preferred salts for use with zinc-dependent enzymes, include, but are not limited to zinc iodate ($Zn(IO_3)_2$), zinc sulfite ($ZnSO_3$), zinc oxalate ($ZnC_2O_4$) and combinations thereof.

Other salts can be used to control enzymatic processes provided they have low solubility in water and can provide controlled release from the polymer. Preferably the salts exhibit increased solubilities at higher temperatures.

Magnesium oxalate ($MgC_2O_4$) is a particularly preferred salt for $Mg^{2+}$-dependent enzymatic processes, such as PCR. $MgC_2O_4$ is difficult to dissolve in water in view of its low solubility at ambient temperatures. For example, at 18° C., $MgC_2O_4$ has a solubility in water of $5.7 \times 10^{-4}$ mol/L. However, $MgC_2O_4$ is nearly 10 times more soluble at 100° C. ($5.4 \times 10^{-3}$ mol/l; Ignatov et al., Russian Journal of Bioorganic Chemistry, Vol. 29, No. 4, pp. 368-371, 2003). Consequently, a composition containing a poorly soluble magnesium salt (such as $MgC_2O_4$) and a substantially water-soluble, water-permeable polymer can increase the specificity of PCR reactions by preventing free $Mg^{2+}$ release at lower temperatures (to activate Taq DNA polymerase), while promoting temperature-dependent release of free magnesium ions (e.g., at 72° C.) and selection of specifically bound primers for Taq DNA polymerase-catalyzed extension.

The amount of salt in the composition of the present invention will depend on e.g., the amount of free ionic enzymatic reactant required for a particular enzymatic process. Enzymatic conditions are widely published and routinely available to those of skill in the art. In addition, they can be empirically determined and/or routinely optimized. Accordingly, when seeking to control an enzyme activity, salt amounts may be empirically determined based on the degree of salt sequestration by the polymer, solubility of the salt, amount of free ionic enzymatic reactant necessary for the enzymatic process and/or the effects of reaction conditions (e.g., temperature, pH, etc.) on the above.

For PCR processes employing heat-stable DNA polymerase enzymes, the amount of magnesium salt associated with the polymer may be empirically determined and may depend on the a variety of factors, including, but not limited to, enzyme reaction volume, amount of free $Mg^{2+}$ necessary for the enzymatic reaction volume, salt release characteristics of the polymer, salt solubility and dissociation characteristics, salt release and dissociation characteristics as a function of temperature and/or pH, molecular weight of salt, etc. Small reaction tubes (e.g., 20, 50-, 100-, 200-, 500-μl Eppendorf tubes) for PCR reactions may accommodate a range of magnesium salt quantities. By way of example, where poly(vinyl butyral-co-vinyl alcohol-co-vinyl acetate is the polymer, the amount of magnesium oxalate for PCR reactions may range from 0.003-10 mg per reaction tube per 100 μl reaction volume. A preferred amount of magnesium oxalate/reaction tube/per 100 μl reaction volume may be 0.1-5 mg-, more preferably 0.1-0.5 mg- and still more preferably 0.1 mg/reaction tube/100 μl reaction volume. Equivalent molar amounts may be determined for other poorly soluble magnesium salts, depending on e.g., the factors outlined above and may be further optimized by empirical determination.

In a further aspect, the present invention provides a reaction vessel or reaction kit for controlling an enzymatic process. The vessel or kit may include a first reaction vessel containing a water-insoluble/water-permeable polymer and an ionic enzymatic cofactor necessary for completing an enzymatic process. The first reaction vessel may further include one or more additional reaction components to facilitate the enzymatic process. Alternatively, the reaction kit may include a plurality of additional reaction vessels, each containing at least one additional reaction component to facilitate an enzymatic process.

In a preferred embodiment, the present invention provides a reaction kit containing a composition having a water-insoluble/water-permeable polymer and a salt of an ionic enzymatic reactant. The composition may be coated on the wall of a reaction vessel (such as a tube, well or plate). The polymer and the salt can be suspended in a suitable solvent, e.g., chloroform. In a particularly preferred embodiment, the polymer/salt suspension is coated onto a wall surface of a reaction vessel by lyophilization.

The coated reaction vessel may be a small reaction tube, such as an Eppendorf tube (having e.g., 20, 50-, 100-, 200-, 500 µl reaction volume capacities etc.), or it may be a larger tube, such as a test tube, where preparative levels are desired. The coated reaction vessel may also be a microtiter plate containing a plurality of wells, each well coated with a polymer/salt mixture. The coated reaction vessel may also be a slide useful in microarray technologies. The size of the vessel or reaction tube can be modified, depending on the scope or sensitivity of the enzymatic process. Essentially any shape or size of vessel can be used according to conventional enzymatic procedures.

Optimal amounts of resin/salt for coating a reaction vessel may be empirically determined for a given application and will depend on the ionic reactant requirements for a particular enzymatic process. In a preferred embodiment, a polymer/salt suspension (in e.g., chloroform) is added to a reaction vessel and dried. The suspension can then be air dried. Alternatively, it can be dried under vacuum pressure (e.g., speed vac) and/or dried for e.g., 10 min at 50° C. or higher.

The coated reaction vessel may be part of a reaction kit further containing one or more reaction components to facilitate an enzymatic process. In one aspect, the contents of a coated reaction tube may be resuspended in a reaction medium containing one or more additional reaction components to facilitate an enzymatic process. The additional reaction components may include e.g., enzyme buffers, salts, cofactors and/or substrates for completing an enzymatic process. By way of example, PCR processes in accordance with the present invention may include at least one DNA polymerase, deoxyribonucleoside triphosphates, at least two primers, at least one target nucleic acid sequence or combinations thereof. Additional reaction components may be incorporated, including markers or dyes (e.g., bioluminescent, chemiluminescent etc.) to provide a qualitative or quantitative read-out of the enzymatic process.

The additional reaction components may be included in the coated reaction vessel prior to resuspension, or they may be contained in one or more additional reaction vessels supplied with a given reaction kit. Thus, a given reaction kit may include a plurality of additional reaction vessels, each containing at least one additional reaction component to facilitate an enzymatic process.

Reaction vessels coated with polymer/salt mixtures may be used interchangeably with a variety of enzymes having different cofactor/substrate requirements for optimal activity. It has been observed that Taq DNA polymerase requires lower $Mg^{2+}$ amounts for optimal activity in PCR (1.5-3.0 mM) compared to other PCR polymerase enzymes, such as Klentaq, which typically require higher free $Mg^{2+}$ concentrations (e.g., 3-4 mM). Consequently, additional salts may be added to a reaction medium to influence the dissociation and/or release of the ionic enzymatic reactant necessary for the enzymatic reaction. Typically, the additional salt shares a common anion with the poorly soluble first salt which can serve to fine-tune (or reduce) the overall levels of freely available ionic salt for driving the enzymatic process.

Ammonium oxalate ($(NH_4)_2C_2O_4$) is an exemplary salt that can be used in conjunction with oxalate-containing salts, such as $MgC_2O_4$ to fine-tune the level of ionic enzymatic reactant released for an enzymatic process. At 25° C., the solubility of $(NH_4)_2C_2O_4$ in water is 124-fold higher compared to $MgC_2O_4$. Consequently, the addition of more highly soluble oxalate salts, e.g., $(NH_4)_2C_2O_4$, may provide a balancing effect on the final concentration of $Mg^{2+}$ released from the poorly soluble $MgC_2O_4$ salt.

By way of example, $(NH_4)_2C_2O_4$ may be included in an enzymatic reaction medium to optimize the levels of freely available $Mg^{2+}$ ions for controlling, in this case, a $Mg^{2+}$-dependent enzymatic process, such as PCR. In one example, $(NH_4)_2C_2O_4$ may be included at a final concentration of e.g., 10-12 mM to reduce the effective amount of freely available $Mg^{2+}$ released in certain PCR hot-start reactions involving e.g., Taq DNA polymerase, which requires a lower $Mg^{2+}$ concentration than Klentaq.

The secondary salt may be provided in the form of a reaction buffer concentrate. For example, a suitable I Ox reaction buffer to use in association with polymer resin/$MgC_2O_4$ mixtures for PCR reactions may include 300 mM KCl, 200 mM Tris-HCl (pH=9.0 at 25C), 100 mM $(NH_4)_2C_2O_4$, 1% Triton X-100. Secondary salt buffers for use with other salts and/or for controlling other enzymatic processes may be prepared in an analogous fashion. Generally, the buffer will be compatible with the enzymatic reaction conditions and will include a more soluble (secondary) salt sharing a common counter-ion with the poorly soluble salt of the ionic reactant entrapped by the polymer.

In a further aspect, the compositions, reaction vessels or kits of the present invention are used in methods for controlling an enzymatic process wherein a composition containing a water-insoluble, water-permeable polymer and a poorly soluble salt containing an ionic enzymatic reactant are contacted with additional reaction component(s) in an aqueous reaction medium, including at least one enzyme. The composition of the reaction components and the reaction conditions (temperature, pH, etc) are adjusted to permit sequestration of the ionic enzymatic reactant under a first reaction condition and release of the ionic enzymatic reactant into the surrounding reaction medium under a second reaction condition (e.g., increased temperature) to activate and/or complete an enzymatic process.

Preferred enzymatic processes include those requiring an ionic enzymatic reactant that can be formulated in a salt. The ionic enzymatic reactant may be a cofactor necessary for initiating or completing an enzymatic process, such as a metal ion. However, a salt of the ionic reactant may also include a metal ion that is not directly involved in the enzymatic process. In this case, the metal ion may merely affect the dissociation and/or release from the polymer of a counter-ion (e.g., ATP, Coenzyme A etc) directly involved in the enzymatic process.

Metal ions participate in numerous metabolic processes and play essential roles in about one third of enzymes (for reviews, see e.g., Nelson, EMBO J., Vol. 18, No. 16, pp. 4361-4371, 1999; Glusker et al., Rigaku K., Vol. 16, No. 2, 1999). Examples of metal ions required for various enzymatic processes include, but are not limited to $Mg^{2+}$, $Mn^{2+}$, $Zn^{2+}$, $Ca^{2+}$, $Cd^{2+}$, $Cu^{2+}$, $Co^{2+}$, $Cr^{2+}$, $Cr^{3+}$, $Cr^{6+}$, $Ni^{2+}$, $Ni^{3+}$, $Pb^{2+}$, $Pb^{4+}$, $Fe^{2+}$, $Fe^{3+}$ and $Hg^{2+}$. Controlled release of the metal ion (or by extension, its counter-ion) can be provided by incorporating a poorly water-soluble metal ion salt.

In one aspect, the present invention provides methods and reaction vessels for controlling an enzymatic process. Preferred enzymes include those used for molecular biology applications. Further information concerning enzymes for molecular biology applications can be found in e.g., "LabFax: Molecular Biology," T. A. Brown (Ed.), Academic Press, 1991; "Methods in Molecular Biology: Vol. 16—Enzymes of Molecular Biology," M. M. Burrell (Ed.), Humana Press, 1993; and "Current Protocols in Molecular Biology," F. M. Ausubel et al. (Eds.), John Wiley and Sons, Inc., 1998).

In a preferred embodiment, the present invention provides methods and reaction vessels for controlling $Mg^{2+}$-dependent enzymes. By way of example, surrounding the poorly water-soluble $Mg^{2+}$-containing salt, such as magnesium oxalate, in a water-insoluble, water-permeable polymer, such as poly(vinyl butyral-co-vinyl alcohol-co-vinyl acetate, the present invention can provide temperature regulated, controlled release of free $Mg^{2+}$ ions for $Mg^{2+}$-dependent enzymatic processes, such as PCR. Thus, in addition to the increased temperature requirement for release of free $Mg^{2+}$ ions, the polymer provides a further means of controlling the availability of free $Mg^{2+}$ ions to activate and/or complete the enzymatic process. Preferably, appreciable amounts of $Mg^{2+}$ ions are not released until after the reaction mixture has incubated for at least about five minutes at 94° C.

$Mg^{2+}$-dependent enzymes that may be controlled in accordance with the present invention include a variety of enzyme members or species defined by the several generic enzyme classes, including DNA polymerases, RNA polymerases, reverse transcriptases, DNA ligases, endonucleases, restriction endonucleases, kinases, and proteases. $Mg^{2+}$-dependent enzymes may originate from a wide variety of animal, bacterial or viral sources, and may be synthesized from native genetic structures or from variants genetically modified by e.g., mutagenesis or genetically modified to express fusion proteins, carrying multiple, distinct functional domains.

Additional examples of $Mg^{2+}$-dependent enzymes include DNA polymerases, such as Klenow fragment and DNA Pol I; reverse transcriptases (RT), such as AMV RT and MMLV RT; most restriction endonucleases; ribonucleases, such as RNase H; and topoisomerases, such as Topoisomerase I.

Some enzymes can alternatively use other metal ions in place of $Mg^{2+}$. For example, RNA polymerases, such as RNA polymerase I or T7-, SP6-, and T4 RNA polymerases can use $Mg^{2+}$ or $Mn^{2+}$. Bal31 nuclease can use either $Mg^{2+}$ or $Ca^{2+}$. DNase I can utilize a variety of different metal ions, including $Mg^{2+}$, $Mn^{2+}$, $Ca^{2+}$, $Co^{2+}$ or $Zn^{2+}$.

Enzymes for use in the present invention may be preferably selected or engineered on the basis of retaining enzymatic stability under a range of reaction conditions affecting release of ionic enzymatic reactants, including high temperatures and/or various pH conditions (high/low, etc.). Particularly preferred enzymes include thermostable and/or pH resistant enzymes.

Thermostable enzymes may be isolated from thermophilic bacterial sources (e.g., thermophilic genus *Thermus*) or they may be isolated and prepared by recombinant means. Representative species of the *Thermus* genus include *T. aquaticus, T. thermophilus, T. rubber, T. filiformis, T. brockianus* and *T. scotoductus*. The thermostable enzymes for use in the present invention may be derived from a broad range of enzyme types.

Examples of thermostable enzymes for use in the present invention, include, but are not limited to: thermostable DNA polymerases disclosed in e.g., U.S. Pat. Nos. 4,889,818, 5,079,352, 5,192,674, 5,374,553, 5,413,926, 5,436,149, 5,455,170, 5,545,552, 5,466,591, 5,500,363, 5,614,402, 5,616,494, 5,736,373, 5,744,312, 6,008,025, 6,027,918, 6,033,859, 6,130,045, 6,214,557; thermostable reverse transcriptases disclosed in e.g., U.S. Pat. No. 5,998,195 and U.S. 2002/0090618; thermostable phosphatases disclosed in e.g., U.S. Pat. Nos. 5,633,138, 5,665,551, 5,939,257; thermostable ligases disclosed in e.g., U.S. Pat. Nos. 5,494,810, 5,506,137, 6,054,564 and 6,576,453; thermostable proteases disclosed in e.g., U.S. Pat. Nos. 5,215,907, 5,346,820, 5,346,821, 5,643,777, 5,705,379, 6,143,517, 6,294,367, 6,358,726, 6,465,236; thermostable topoisomerases disclosed in e.g., U.S. Pat. Nos. 5,427,928 and 5,656,463; thermostable ribonucleases disclosed in e.g., U.S. Pat. Nos. 5,459,055 and 5,500,370; thermostable beta-galactosidases disclosed in e.g., U.S. Pat. Nos. 5,432,078 and 5,744,345; thermostable restriction endonucleases, including e.g., Acc III, Acs I/Apo I, Acy I, Bco I, BsaBI/BsiBI, BsaMI, BsaJI, BsaOI, BsaWI, BscBI, BscCI, BscFI, BseAI, BsiC1, BsiE1, BSi HKAJ, BsiLI, BsiMI, BsiQI, BsiWI, BsiXI, BsiZI, Bsi I, Bsm I, BsmAI, BsmBI, Bss, T11, Bsr1, BsrD1, Bsi711, BsiB1, BsiN1, BsiU1, BsiY1, BsiZ1, Dsa 1, Mae 11, Mae 111, Mwo 1, Ssp B1, Taq I, Taq II, Taq52 I, Tfi I, Tru91, TspE1, TspRI, Tsp45 I, Tsp4C I, Tsp509 I, Tth111 II; Flap endonuclease disclosed in U.S. Pat. No. 6,251,649; and FLPe, a mutant, thermostable recombinase of Flp (Bucholz et al., Nature Biotechnology, Vol. 16, pp. 657-662, 1998).

Preferred $Mg^{2+}$-dependent enzymes include, but are not limited to thermally stable enzymes. Thermostable $Mg^{2+}$-dependent enzymes may include thermostable DNA polymerases, RNA polymerases, reverse transcriptases, DNA ligases, endonucleases, restriction endonucleases, kinases, and proteases, including, but not limited to the aforementioned enzymes above. Thermally stable enzymes may be isolated from thermophilic bacterial sources or they may be isolated and prepared by recombinant means.

Preferred DNA polymerases for use in PCR applications include thermally stable DNA polymerases and/or combinations thereof. Thermally stable DNA polymerases may include, but are not limited to, *Thermus aquaticus* DNA polymerase; N-terminal deletions of Taq polymerase, including the Stoffel fragment of DNA polymerase, Klentaq-235, and Klentaq-278; *Thermus thermophilus* DNA polymerase; *Bacillus caldotenax* DNA polymerase; *Thermus flavus* DNA polymerase; *Bacillus stearothermophilus* DNA polymerase; and archaebacterial DNA polymerases, such as *Thermococcus litoralis* DNA polymerase (also referred to as Vent$_R$®), Pfu, Pfx, Pwo, and DeepVent$_R$® or a mixture thereof. Other commercially available polymerases DNA polymerases include TaqLA or Expand High Fidelity$^{Plus}$ Enzyme Blend (Roche); KlenTaqLA, KlenTaq1, TthLA (Perkin-Elmer), ExTaq® (Takara Shuzo); Elongase® (Life Technologies); Taquenase™ (Amersham), TthXL (Perkin Elmer); Advantage™ KlenTaq and Advantage™ Tth (Clontech); TaqPlus® and TaqExtender™ (Stratagene); or mixtures thereof.

In a preferred embodiment, the present invention includes compositions and methods for increasing the specificity of PCR. Specifically, the present invention provides processes and kits for performing a hot-start PCR. The processes and kits utilize the step of sequestering magnesium ions in a water-insoluble, water-permeable polymer, rendering a DNA polymerase largely inactive until the temperature of the reaction medium is raised to solubilize and release the magnesium ions from the sequestering polymer so they can activate the polymerase. By limiting the activity of the DNA polymerase enzyme for PCR until the extension cycle in which polymerization is desired, amplification specificity of target DNA molecules is increased with minimal or no formation of competitive or inhibitory products.

The present reaction composition can be applied to PCR processes as set forth in e.g., Examples 1, 4 and 5 below, using otherwise conventional PCR methodologies (see e.g., PCR Protocols: A Guide To Methods And Applications, M. A. Innis (ed.), Academic Press, Inc., 1990; PCR Technology: Principles And Applications For DNA Amplification, H. A. Erlich (ed.), Oxford University Press, Inc., 1992; Current Protocols in Molecular Biology, F. M. Ausubel et al. (Eds.), John Wiley and Sons, Inc., 1998).

The scope of the present invention further includes compositions and methods for controlling enzymes requiring other metal ions for activity. By way of example, $Zn^{2+}$ is an ionic enzymatic reactant for S1 nuclease, Mung Bean nuclease and Alkaline phosphatase. Alkaline phosphatase may further utilize other metal ions, such as $Mg^{2+}$, $Mn^{2+}$, $Co^{2+}$ or $Hg^{2+}$. $Ca2+$ is an ionic reactant for S7 nuclease. $Co^{2+}$ is an ionic reactant for Terminal Deoxynucleotidyl Transferase (TdT) and for eukaryotic methionyl aminopeptidase (Proc. Natl. Acad. Sci., Vol. 92, pp. 7714-7718, Aug. 1995). $Cd^{2+}$ is an ionic reactant for dimerization and transcription factor binding to metallothionein promoters (Biochemistry, Vol. 31, No. 7, pp. 2181-2186, Feb. 25, 1992. $Pb2+$ is an ionic reactant for ribozyme-medicated RNA cleavage process catalyzed by leadzyme (Wedekind et al., Biochemistry, Vol. 42, No. 32, pp. 9554-9563, Aug. 19, 2003).

Tth DNA polymerase can utilize $Mn^{2+}$ in place of $Mg^{2+}$ to enhance its reverse transcriptase activities (Myers et al., Biochemistry, Vol. 30, No. 31, Aug. 6, 1991). Thus, in a variation of the present example directed to control of $Mg^{2+}$-dependent enzymes using Mg-oxalate, the reverse trancriptase activity of Tth DNA polymerase may be controlled by an analogous process using an water-insoluble, water-permeable polymer resin, such as poly(vinyl butyral) in combination with a poorly water-soluble $Mn^{2+}$ salt, such as manganese II oxalate, manganese II iodate or manganese II tungstate.

The principles, methodologies and examples described herein (and below) for controlling $Mg^{2+}$-dependent DNA polymerase activity may be applied in an analogous fashion to control other types of $Mg^{2+}$-dependent- or $Mg^{2+}$-independent enzymes described above. Such enzymes may be similarly controlled where the metal ion required for activity originates from magnesium, manganese, cadmium, calcium, cobalt, copper, iron, lead, molybdenum, mercury, nickel or zinc. Preferred ionic reactants include, but are not limited to $Mg^{2+}$, $Mn^{2+}$, $Zn^{2+}$, $Ca^{2+}$, $Cd^{2+}$, $Cu^{2+}$, $Co^{2+}$, $Cr^{2+}$, $Cr^{3+}$, $Cr^{6+}$, $Ni^{2+}$, $Ni^{3+}$, $Pb^{2+}$, $Pb^{4+}$, $Fe^{2+}$, $Fe^{3+}$ and $Hg^{2+}$. Preferred monovalent cations may include, but are not limited to $Na^+$, $K^+$ and $NH_{4+}$.

The principles for controlling metal ion-dependent enzymatic processes may be similarly extended to enzymatic processes requiring other ionic reactants including but not limited to, ATP, ADP, pyrophosphate, coenzymes, Nicotinamide Adenine Dinucleotide (NAD+), Nicotinamide Adenine Dinucleotide Phosphate ($NADP^+$), Coenzyme A, Coenzyme $B_{12}$, Coenzymes $Q_{1-10}$, pyridoxal phosphate, thiamine pyrophosphate, nucleotides, deoxynucleotides, ribonucleotides, deoxyribonucleotides, dideoxyribonucleotides, primers and oligonucleotides; anionic radicals; and the like.

The following examples illustrate aspects of the invention.

EXAMPLES

Example 1

Control of DNA Polymerase Activity for PCR

1. Preparation of magnesium oxalate/butyral resin suspension. 1 gram of magnesium oxalate was suspended in 1 ml of butyral resin solution (0.05 g/ml in chloroform). 5 µl of the resulting suspension was added to a small reaction tube. The suspension was dried for 10 min. at 50° C. A separate tube was prepared as a control having 5 µl magnesium oxalate solution (1 g/ml chloroform) without the butyral resin.

2. Addition of reaction components for PCR reaction. A 100 µl PCR reaction mixture (10 mM Tris-HCl, pH 9.0 at 25° C.; 50 mM KCl; 0.1% Triton X-100; 0.2 mM deoxyribonucleoside triphosphates (dNTPs); primers P1 and P2 (20 pmol each); 100 ng of E. coli DNA as a template; and 10 U Klentaq polymerase) was added to reaction tubes containing the magnesium oxalate/butyral resin or the magnesium oxalate control. Primers P1 (5'-ATGGCTAACGAATTAAC-CTGGCA, SEQ ID NO. 1) and P2 (5'-TTACTCACTCTCT-GCCGGTAAT, SEQ ID NO. 2) were designed to amplify a 690 bp DNA fragment from the E. coli Uracil DNA glycosylase gene.

Figure 1:
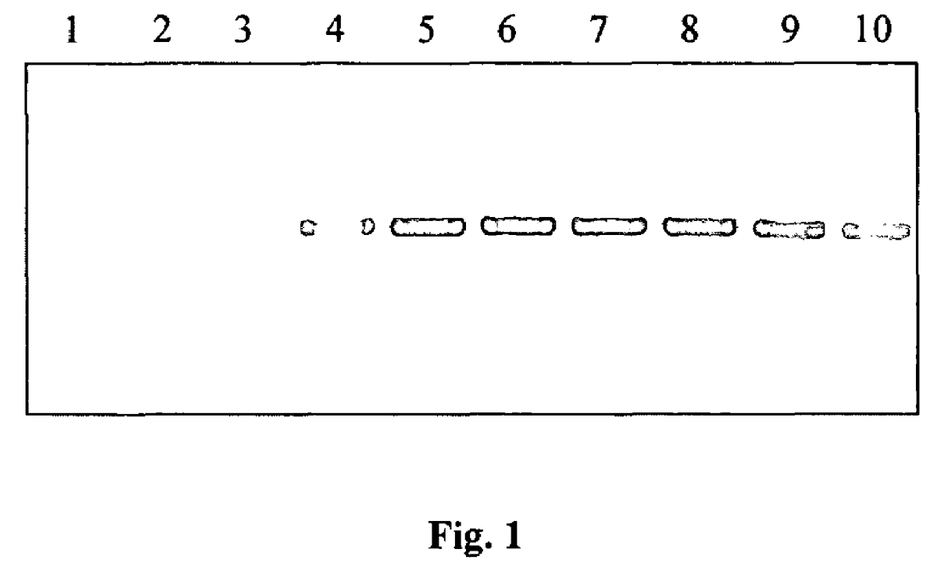
FIG. 1 depicts an electrophoretic analysis of the PCR products obtained in Example 1 using reaction tubes coated with Mg-oxalate embedded in butyral resin (lanes 1 through 5) or using reaction tubes containing Mg-oxalate only (i.e., without butyral resin); lanes 6 through 10. The reaction mixtures were initially incubated at 94° C. for 0 min (lanes 1 and 6), 1 min (lanes 2 and 7) 2 min (lanes 3 and 8), 3 min (4 and 9) and 5 min (5 and 10).

3. PCR reaction conditions and analysis. The reaction mixture was heated from 24° C. to 94° C. at a rate of 1° C./sec. Upon reaching a temperature of 94° C., 15 µl samples were removed at t=0, 1, 2, 3 and 5 minutes. Each of the samples was transferred to a clean tube (without magnesium oxalate and/or resin) and subjected to 25 cycles according to the following reaction conditions: 94° C.-30 sec; 58° C.-30 sec; 72° C.-100 sec. FIG. 1 depicts an electrophoretic analysis of the resulting PCR products obtained. This analysis suggests that an incubation period of at least 3.5 minutes was required to liberate sufficient magnesium ions to activate the polymerase so that amplified PCR products could be detected following 25 cycles (FIG. 1, lane 4). The lag period observed reflects control over activation of the Klentaq DNA polymerase activity. The amount of magnesium released during the hot-start is sufficient to maintain activity of the enzyme in the subsequent PCR amplification reaction without adding additional magnesium. In contrast, the control reactions showed that without the butyral polymer resin, detectable PCR products could be obtained without any incubation at 94° C. This suggests that absent sequestration of the magnesium ions by the butyral resin, the polymerase was active even before attaining a temperature of 94° C.

Example 2

Control of Restriction Endonuclease Digestion

1. Preparation of magnesium oxalate/butyral resin-coated reaction tubes. Magnesium oxalate/butyral resin-coated reaction tubes were prepared as described in Example 1.

2. Addition of reaction components for restriction endonuclease digestion. A 100 μl restriction enzyme digestion mixture (100 mM NaCl; 10 mM Tris-HCl (pH 8.4 at 25° C.); 10 mM 2-mercaptoethanol; 2 μg DNA pBR322; 2 U Taq I restriction endonuclease was added to each of the reaction tubes containing the magnesium oxalate/butyral resin.

Figure 2:
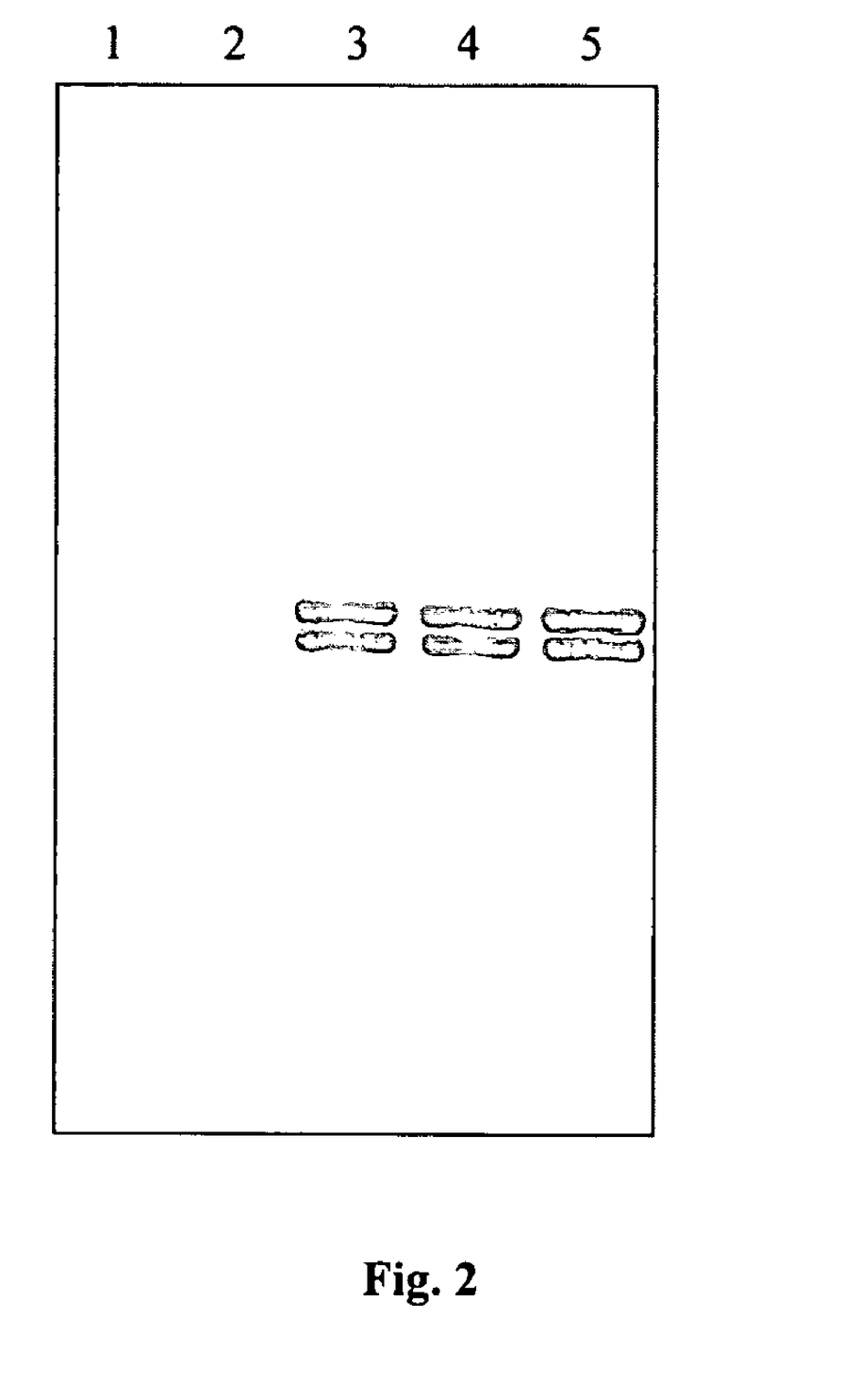
FIG. 2 depicts an electrophoretic analysis of DNA fragments obtained following restriction endonuclease digestion of pBR322 using Taq I as described in Example 2. The restriction digestion mixtures were initially incubated at 64° C. for 0 min (lane 1), 1 min (lane 2), 2 min (lane 3), 3 min (lane 4) and 5 min (lane 5).

3. Restriction endonuclease digestion conditions and analysis. The reaction mixtures were heated from 24° C. to 64° C. at a rate of 0.5° C./sec. After incubation at 64° C. for t=0, 1, 2, 3 and 5 minutes, 15 μl samples were removed and placed into clean reaction tubes (without magnesium oxalate). Incubation in the reaction tubes was continued for 1 hr at 64° C. FIG. 2 is an electrophoretic analysis of the digestion products indicating that activation of restriction endonuclease activity required at least a 2 min. incubation at 64° C. This initial incubation time is sufficient to release enough magnesium into the reaction to maintain activity of the restriction enzyme during the length of the continued reaction without adding additional magnesium.

Example 3

Control of DNA Ligase Activity

Preparation of magnesium oxalate/butyral resin-coated reaction tubes. Magnesium oxalate/butyral resin-coated reaction tubes were prepared as described in Example 1.

Figure 3:
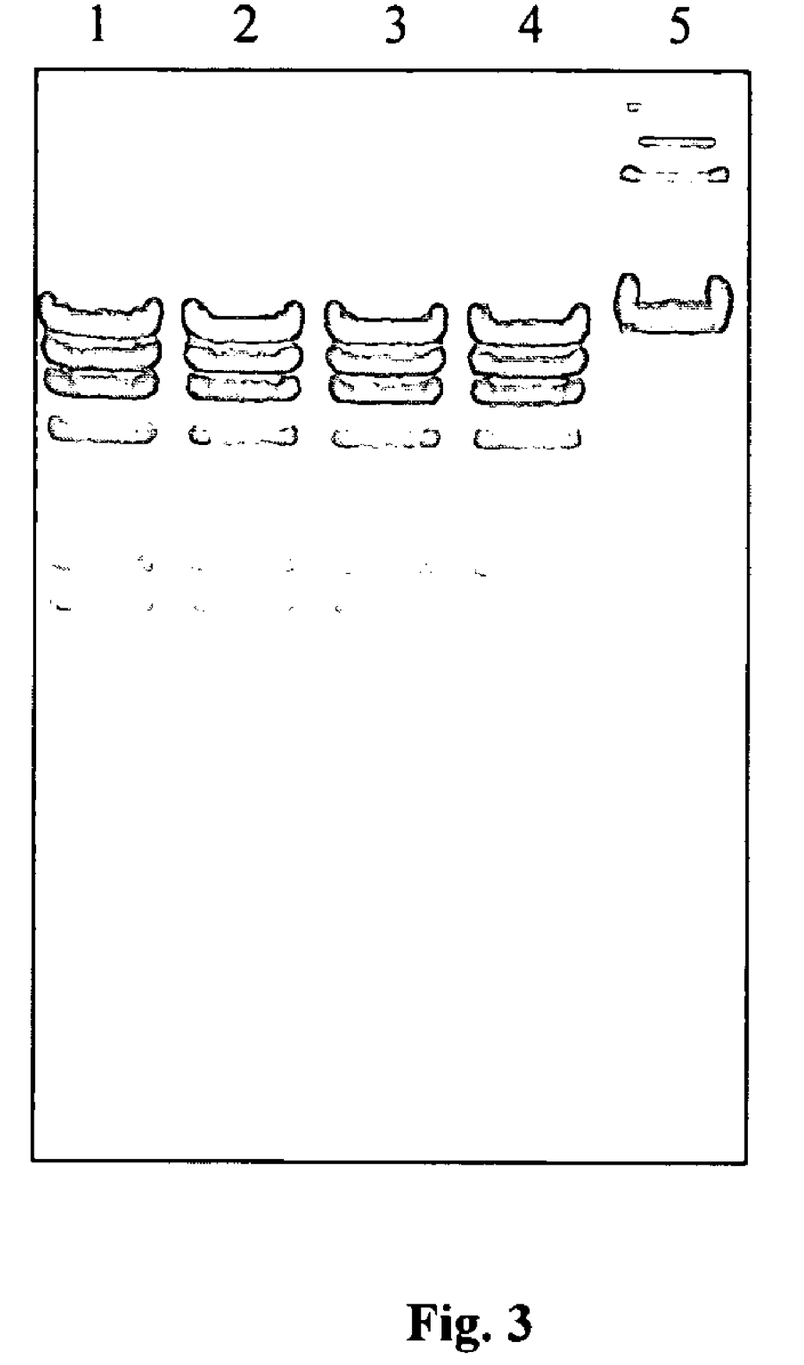
FIG. 3 depicts an electrophoretic analysis of DNA ligation products obtained in Example 3. Following addition of T4 DNA ligase to Mg-oxalate-containing tubes, the reaction mixtures were incubated initially at 30° C. for 1 min (lane 1), 2 min (lane 2), for 3 min (lane 3), for 5 min (lane 4) and 10 min (lane 5).

100 μl of a DNA ligase reaction mixture (50 mM Tris-HCl (pH 8.0 at 25° C.); 10 mM 2-mercaptoethanol; 1 mM ATP; 2 μg lambda DNA digested with Hind III; 2 Weiss units of T4 DNA ligase) was added to the prepared reaction tubes. Following incubation of the magnesium oxalate-containing tube with the DNA ligase reaction mixture at 30° C. for t=1, 2, 3, 5 and 10 min., 15 μl samples were removed to clean tubes (without magnesium oxalate) and incubation proceeded for an additional hour at 30° C. Electrophoretic analysis indicated that an incubation time of 10 min at 30° C. was needed to allow enough magnesium to diffuse from the resin in order to activate T4 DNA ligase (FIG. 3, lane 5).

Example 4

Figure 4:
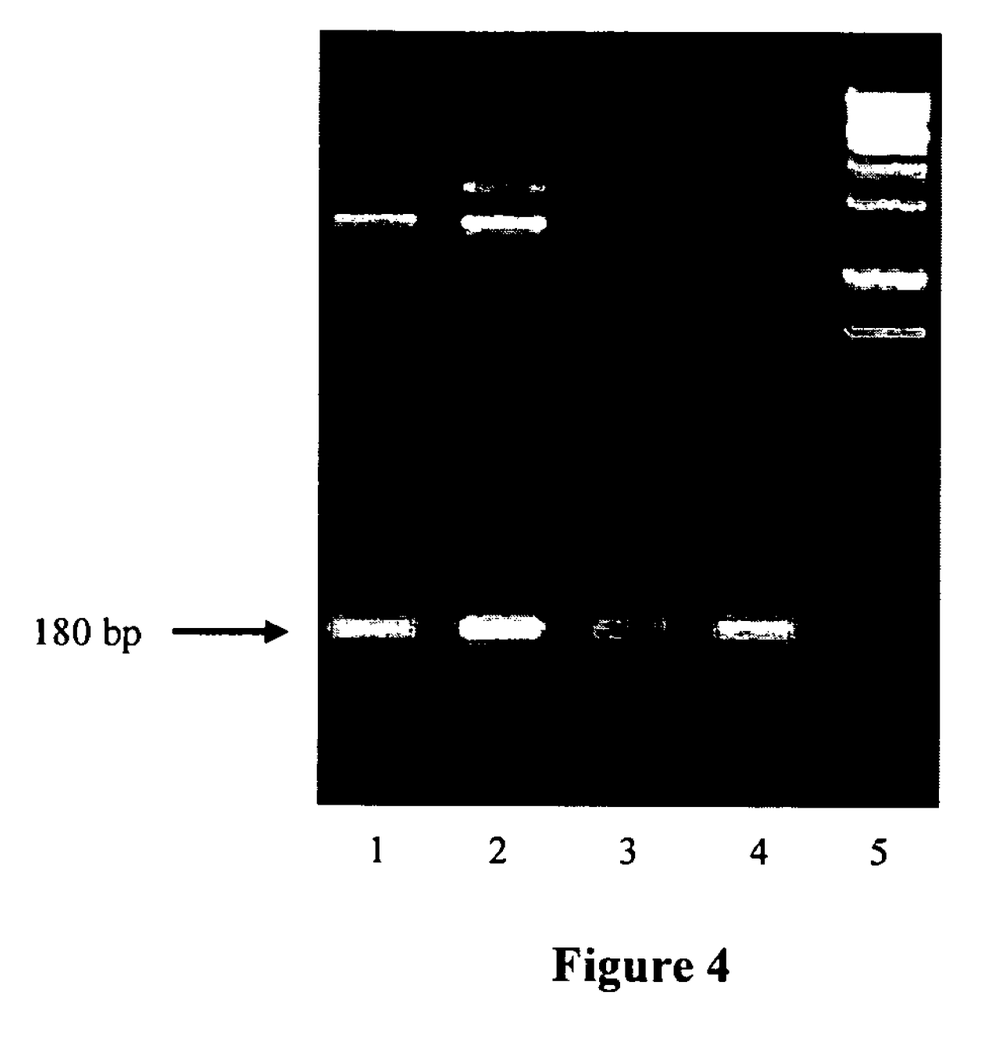
FIG. 4 depicts an electrophoretic analysis of PCR products amplified from 50 ng of human genomic DNA. A manual hot-start was performed by adding Taq DNA polymerase enzyme (lane 1, 0.5 U; lane 2, 2.0 U) to a 25 μl preheated (94° C., 5 min.) reaction mixture. The resulting reaction mixture was subjected to standard PCR cycling conditions (lanes 1 and 2). For comparison, full 25 μl reaction mixtures containing Taq DNA polymerase enzyme (lane 3, 0.5 U; lane 4, 2.0 U) were added to the reaction tubes coated with polymer and salt and subjected to standard PCR cycling conditions (lanes 3 and 4).

Increased Specificity of PCR Using Coated Reaction Tubes Compared to Conventional PCR Approaches A. Comparison to Conventional PCR Hot-Start Reaction A 180 bp DNA fragment was amplified from 50 ng of human genomic DNA for 30 cycles. The following reaction conditions were compared. A manual hot-start was performed by adding Taq DNA polymerase enzyme (FIG. 4, lane 1, 0.5 U; lane 2, 2.0 U) to a 25 μl reaction mixture preheated 5 min. at 94° C. and subjected to standard PCR conditions (lanes 1 and 2). For comparison, complete 25 μl reaction mixtures containing Taq DNA polymerase enzyme (lane 3, 0.5 U; lane 4, 2.0 U) was added to the coated reaction tubes of the present invention. The complete reaction mixtures were preheated 5 min. at 94° C. and subjected to the same PCR conditions used in lanes 1 and 2. FIG. 4 depicts an electrophoretic analysis of the amplification products obtained. Compared to the manual hot-start procedure, fewer non-specific amplification products were obtained when using coated reaction tubes (see absence of higher molecular weight amplification products in lanes 3, 4 compared to lanes 1, 2).

B. Amplification of 1.2 kb *Xenopus laevis* Promoter Region

Figure 5:
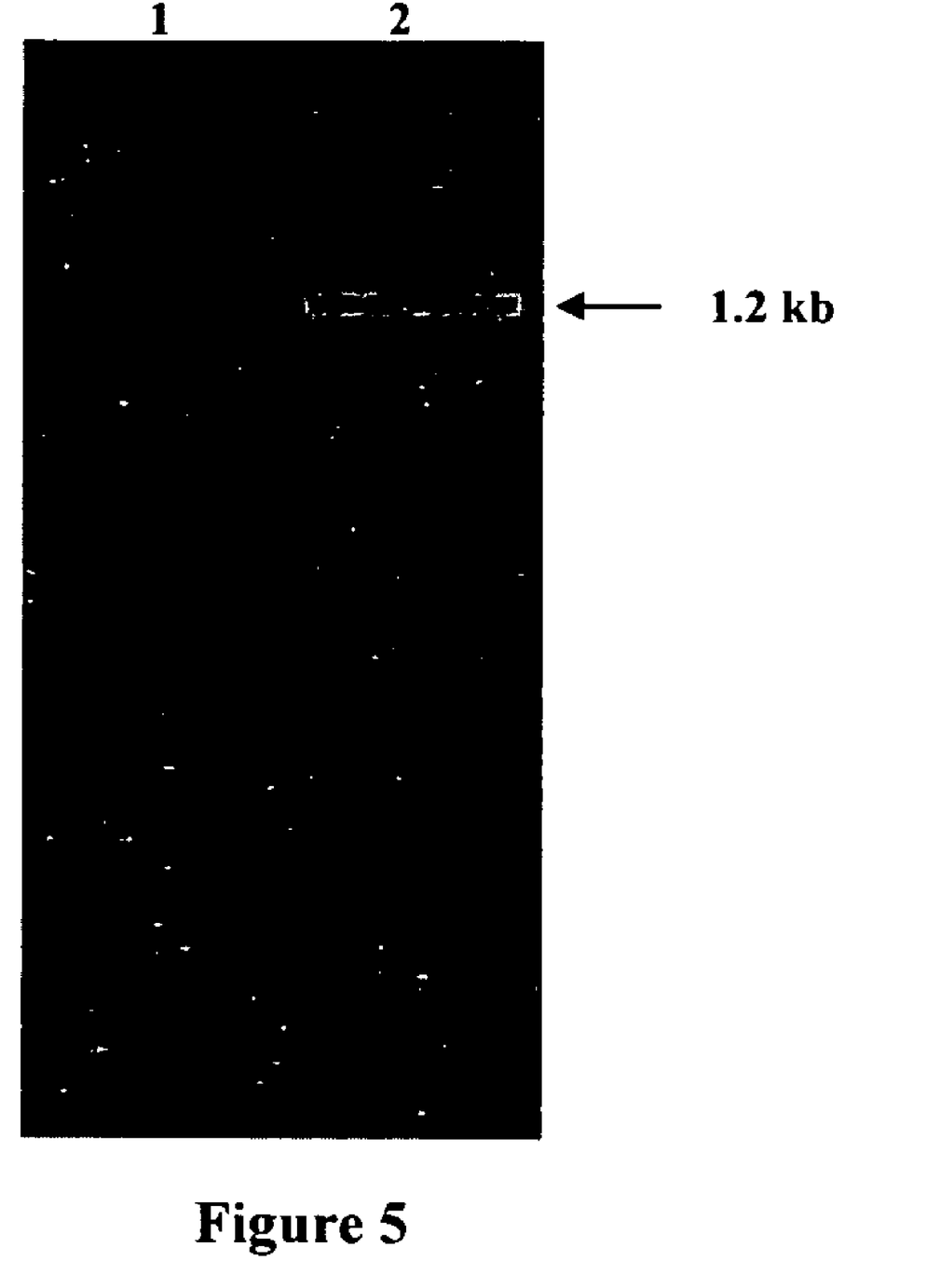
FIG. 5 depicts an electrophoretic analysis of amplification products obtained when amplifying 20 ng of South African frog *Xenopus laevis* genomic DNA to produce a 1.2 kb fragment from a promoter region of the *Xenopus laevis* gene XAC-2. Conventional (lane 1) and coated reaction tubes (lane 2) were used following standard PCR cycling conditions.

Using appropriately designed primers under conventional PCR cycling conditions (e.g., 30 cycles), a 1.2 kb fragment of a promoter region of the *Xenopus laevis* gene XAC-2 was amplified from 20 ng of a South African frog *Xenopus laevis* genomic DNA library. PCR reactions were prepared in conventional reaction tubes (lane 1) and in coated reaction tubes (lane 2). FIG. 5 depicts an electrophoretic analysis of the amplification products obtained. Under these reaction conditions only the coated reaction tubes provided detectable levels of the desired product (lane 2). When using conventional tubes smaller, non-specific products were obtained (lane 1).

It is to be understood that the above-described compositions and methods are merely representative embodiments illustrating the principles of this invention and that other variations in the compositions and methods may be devised by those skilled in the art without departing from the spirit and scope of this invention.

What is claimed:

1. A method for activating an enzymatic process comprising:
   providing a composition comprising at least one substantially water-insoluble, water-permeable polymer and at least one salt of an ionic enzymatic reactant, where the at least one salt is poorly soluble in water; and
   contacting said composition with a reaction medium comprising an enzyme for a time sufficient to release the ionic enzymatic reactant into the reaction medium, thereby activating the enzymatic process.

2. The method of claim 1, further comprising the step of raising the temperature of the reaction medium, thereby stimulating release of the ionic enzymatic reactant.

3. The method of claim 1, where the ionic enzymatic reactant is selected from the group consisting of: magnesium, manganese, cadmium, calcium, cobalt, copper, iron, lead, molybdenum, mercury, nickel, zinc, sodium, potassium and ammonium.

4. The method of claim 1, where the at least one polymer is selected from the group consisting of: butyral resin, polyvinyl acetal, poly(vinyl butyral-co-vinyl alcohol-co-vinyl acetate), polyvinyl butyrate, polyvinyl acetate and combinations and co-monomers thereof.

5. The method of claim 1, where the at least one polymer includes poly(vinyl butyral-co-vinyl alcohol-co-vinyl acetate).

6. The method of claim 1, where the salt has a molar solubility in water at 25° C. of between about $1 \times 10^{-3}$ mol/L and $1 \times 10^{-7}$ mol/L.

7. The method of claim 1, where the salt is selected from the group consisting of: magnesium sulfite, magnesium oxalate, magnesium fluoride, magnesium tungstate, manganese (II) iodate, manganese (II) oxalate, manganese (II) tungstate, calcium tungstate, calcium hydrogen phosphate, calcium sulfite, calcium fluoride, calcium oxalate, calcium hydroxide, calcium iodate, copper (II) fluoride, copper (II) iodate, copper (II) molybdate, copper (I) chloride, copper (II) oxalate, copper (I) bromide, iron (II) oxalate, iron (II) fluoride, lead (II) bromide, lead (II) fluoride, lead (II) iodide, lead (II) thiocyanate, lead (II) tungstate, lead (II) sulfate, lead (II) oxalate, molybdenum (VI) oxide, nickel (II) iodate, nickel (II) carbonate, potassium periodate, sodium tellurate, sodium hexafluorosilicate, zinc iodate, zinc sulfite, zinc oxalate.

8. The method of claim 7, where the at least one salt is magnesium oxalate.

9. The method of claim 1, where the composition comprises poly(vinyl butyral-co-vinyl alcohol-co-vinyl acetate) and magnesium oxalate.

10. The method of claim 1, where the enzyme is a member of the group consisting of: polymerase, ligase, endonuclease, kinase, protease and combinations thereof.

11. The method of claim 1, where the enzyme is a thermostable enzyme.

12. The method of claim 1, where the enzyme is a thermostable DNA polymerase enzyme.

13. A method for activating an enzymatic process comprising:
   providing at least one polymer selected from the group consisting of: butyral resin, polyvinyl acetal, poly(vinyl butyral-co-vinyl alcohol-co-vinyl acetate), polyvinyl butyrate, polyvinyl acetate and combinations and co-monomers thereof; and
   sequestering into a complex with the at least one polymer at least one salt of an ionic enzymatic reactant and a counter-ion to form a composition, wherein the ionic enzymatic reactant is a metal ion, and the at least one salt has a molar solubility in water at 25° C. of between about $1 \times 10^{-3}$ mol/L and $1 \times 10^{-7}$ mol/L; and
   contacting the composition with a reaction medium comprising a thermostable enzyme; and
   stimulating release of the ionic enzymatic reactant from the salt or the at least one polymer, thereby activating the enzymatic process.

14. The method of claim 13, comprising raising the temperature of the reaction medium to stimulate release of the ionic enzymatic reactant into the reaction medium.

15. The method of claim 13, where the counter-ion is oxalate.

16. The method of claim 13, where the complex comprises poly(vinyl butyral-co-vinyl alcohol-co-vinyl acetate) and magnesium oxalate.

17. The method of claim 13, where the thermostable enzyme is a thermostable DNA polymerase enzyme.

18. The method of claim 13, further comprising addition of ammonium oxalate to the enzymatic process.

* * * * *